United States Patent
Bauss et al.

(10) Patent No.: US 6,680,307 B1
(45) Date of Patent: Jan. 20, 2004

(54) USE OF IBANDRONATE FOR PROMOTING OSSEOINTEGRATION OF ENDOPROSTHESES

(75) Inventors: Frieder Bauss, Neuhofen (DE); Andreas A. Kurth, Frankfurt am Main (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/857,035

(22) PCT Filed: Nov. 29, 1999

(86) PCT No.: PCT/EP99/09252

§ 371 (c)(1),
(2), (4) Date: May 31, 2001

(87) PCT Pub. No.: WO00/33849

PCT Pub. Date: Jun. 15, 2000

(30) Foreign Application Priority Data

Dec. 4, 1998 (DE) .......................................... 198 55 976

(51) Int. Cl.[7] .......................... A61K 31/66; A61K 31/19
(52) U.S. Cl. ...................... 514/102; 514/103; 514/104; 514/107; 514/108
(58) Field of Search ................................ 514/102, 103, 514/104, 107, 108

(56) References Cited

U.S. PATENT DOCUMENTS

| 4,927,814 A | 5/1990 | Gall et al. |
| 5,646,134 A | 7/1997 | Yates |
| 6,022,887 A | * 2/2000 | Gasper et al. ............. 514/451 |

FOREIGN PATENT DOCUMENTS

| EP | 0252 504 | 1/1988 |
| WO | WO 94 14455 | 7/1994 |
| WO | WO 94/21266 | 9/1994 |
| WO | WO 94 23770 | 10/1994 |
| WO | WO 95/28936 | 11/1995 |
| WO | WO 95/30421 | 11/1995 |
| WO | WO 96/39107 A1 * | 12/1996 |

OTHER PUBLICATIONS

Hofmann et al., Acta Orthop Scan 68(2):161–166 (1997).
Burke et al., J. Bone Joint Surg. 73BL:33–38 (1991).
The Saege–Schliff Technique, J. Oral Pathology 11:318–326 (1982).
Krüger et al., Orthopädische Praxis 34, 5(1998) 287–293.
Wall et al., Orthopädische Praxis 34, 2(1998) 73–77.

* cited by examiner

*Primary Examiner*—Zohreh Fay
*Assistant Examiner*—Brian-Yong Kwon
(74) *Attorney, Agent, or Firm*—George W. Johnston; Patricia S. Rocha-Tramaloni; Bernard Lau

(57) ABSTRACT

The invention relates to use of ibandronic acid (1-hydroxy-3-(N-methyl-N-pentyl)aminopropyl-1,1-diphosphonic acid) or physiologically compatible salts or esters thereof for improving the osseointegration of cement-free anchored endoprostheses. Ibandronate or salts thereof is applied for a short time immediately after insertion of an endoprosthesis, with the surprising result that secondary stability of the implant is obtained in only 5 weeks or less after the operation.

3 Claims, No Drawings

USE OF IBANDRONATE FOR PROMOTING OSSEOINTEGRATION OF ENDOPROSTHESES

This Application is a 371 of PCT/EP99/09252 filed Nov. 29, 1999.

The invention relates to use of ibandronic acid (1-hydroxy-3-(N-methyl-N-pentyl)aminopropyl-1,1-diphosphonic acid) or physiologically compatible salts or esters thereof for improving the osseointegration of cement-free anchored endoprostheses. Ibandronate or salts thereof is applied for a short time immediately after insertion of an endoprosthesis, with the surprising result that secondary stability of the implant is obtained in only 5 weeks or less after the operation.

Bones serve mainly as a support, and consequently bone is frequently regarded as a simple building material. However, bone is a complicated biomaterial adapted to a wide variety of requirements, stimuli and noxae to which it is exposed. Endoprostheses are available as substitutes for bones and joints. However endoprostheses, even when biomechanically highly refined, do not have an active effect on the environmental and load factors.

Throughout the world, about 1.5 million hip-joint endoprostheses are implanted per year, including about 120,000 in Germany. There is also a considerable number of other joint prostheses, e.g. knee-joint, ankle-joint and shoulder-joint endoprostheses. It is expected that the number of primary-implanted endoprostheses, particularly the number needing to be changed, will continue to increase. Meanwhile even relatively young patients are provided with endoprostheses. The life expectancy of man is progressively increasing, so that in some cases up to 3 or 4 changes of prostheses may be expected for individual patients during their life. Cement-free implants are increasingly used in order to preserve bone substance during the first operation and particularly during any required replacement operations and because of the assumed longer survival time of the prostheses. Younger patients needing an endoprosthesis will profit in particular from this kind of tissue-preserving treatment. Longer-lasting endoprostheses are also necessary in view of increased life expectancy and for economic reasons.

Special consideration must therefore be given to the processes and morphological changes occurring in the time after the operation until final stabilisation of the implant bed in the bone, and to knowledge about the primary and secondary stability, particularly of cement-free endoprostheses, since cement-free anchoring of implants has become the preferred method.

"Primary stability" of an implant is described as the situation directly after implantation of the prosthesis in the bone. The prosthesis, via its distal part, is anchored either in the intramedullary canal in the diaphysis (cortical bone) or in the proximal metaphysis of the trochanter prominence. This primary stability is only qualitative, since the prosthesis is not yet incorporated in the bone.

Secondary stability, particularly in the case of hip prostheses, is usually attained only a few months after the bone grows into the prosthesis surface (osseointegration). In addition therefore to qualitative stabilisation there is a quantitative component, ensuring long-term stability of the prosthesis.

The process from primary stability to secondary stability goes through various phases. The first phase after prosthesis implantation is characterised by partial death of bone. Immediately after the operation, most parts of the neighbouring bone are intact. The subsequent partial bone death occurs over a few millimetres in the immediate neighbourhood of the prosthesis interface (the contact surface between the prosthesis and the bone). Dilated vessels and infiltration of polymorphonucleic cells occurs quickly at the boundary between still-living bone and dead bone, followed by fibroblasts, osteoblasts and osteoclasts. Repair occurs during the next stage. The dead bone tissue is infiltrated by granulation tissue and connective tissue. Macrophages and giant cells are occasionally observed. Newly-formed bone is superposed on the dead bone.

The third phase can last up to 2 years, during which the prosthesis is stabilised. During this time the dead bone material disintegrates and is replaced by woven and lamellar bone. At the end of the reconstruction process a narrow seam of connective tissue is frequently left between the bone and the smooth surface of the prosthesis. These phases are also influenced by the individual characteristics of the patient such as bone metabolism (osteoporotic, osteopenic, juvenile) and extrinsic factors such as relief of stress on the prosthesis after the operation and the form of rehabilitation.

The disadvantages of cement-free anchoring, as opposed to the cemented method, according to existing knowledge is that secondary stabilisation of a prosthesis occurs after a period of not less than 6–8 weeks.

Hofmann et al. (Progression of human bone ingrowth into porous-coated implants. Acta Orthop Scan 1997; 68 (2):161–166 discloses that the secondary stabilising of hip prostheses takes up to 9 months. The results of his study are explained by the fact that the ingrowth of human trabecula bone occurs at a speed of about 1 micrometer per day. The maximum attainable ingrowth of the prosthesis occurs not before 9 months after the operation, even if surface-treated prostheses are used. This agrees with the observation of Krüger et al. (Teilbelastng oder Vollbelastung—Therapiestrategie nach zementfreier Hüfttotalendoprothese Orthop Praxis 1998; 34 (5):287–293). In all cases Krüger noted additional sintering of the prosthesis shank during the first 6 months after the operation, with formation of a delicate sclerosis line in the Gruen zone 1. Also Wall et al. (Auswertung der Osseointegration von zementlosen Hüftprothesenstielen mit Computerauswertung digitaler Röntgendensitometrie Orthop. Praxis 34:73–77 1998) showed a decrease of 18% in the optical density of the bone tissue in all Gruen zones during the first 6 months after the operation, irrespective of which of the two types of prosthesis was investigated. Only thereafter was there a renewed increase of bone density, for 24 months after the operation only a starting value of 92 to 97% had been reached. In many centres, therefore, patients keep the operated leg stress-free for up to 6 months after the operation. This is to prevent the prosthesis sinking further into the bone or causing fractures.

According to Burke et al. (Micromotion of cemented and uncemented femoral components. J Bone Joint Surg 73B:33–38 1991) secondary integration of the bone into the prosthesis, disturbed by pathological micromovements (>150 micrometers) results in formation of connective tissue on the interface between the bone and prosthesis. This, and the resulting fear of fractures, make it necessary to relieve stress on the prosthesis for a prolonged period. This greatly slows the rehabilitation of patients, and may result in more and longer-lasting complaints.

On the other hand, a reduced mechanical load on the bone (stress shielding) results in periprosthetic bone atrophy, which may last up to a year and is regarded as a reason for premature loosening of the cement-free prosthesis.

The operations, the duration of post-operative after-treatment in clinics, the non-productive time during the rehabilitation phase, re-integration of younger patients in the work progress and subsequent operations result in enormous costs to the community.

The main proposals hitherto for improving the early and long-term results after endoprosthetic replacement are: improving the design of prostheses with proximal introduction of force, rotational stability, surface coatings and press fit of cement-free endoprostheses. In present clinical treatment there is no use of drugs for increasing the ingrowth of endoprostheses, although the use of growth factors (e.g. BMPs) in conjunction with cement-free implants has been studied in recent research (Proceedings of the annual meeting of the ORS 5, 245, 339, 599 1998 New Orleans).

On the other hand drugs from the amino-bisphosphonate group have a positive influence on "bone remodelling" and produce an increase in bone mass and bone quality, particularly in osteoporosis research. Pre-clinical knowledge of biological and physical properties of bisphosphonates has been available for about 30 years.

Each bisphosphonate has its own chemical, biological and physiological properties and consequently its own activity profile. Bisphosphonates can be used inter alia in bone surgery.

For example, use of bisphosphonates in bone surgery is known from WO 94/21266 A1. Clodronate in particular is used before and/or after a transplantation operation to increase the formation of bone tissue and/or to eliminate complications after implantation. A daily dose of 0.01–100 mg/kg is disclosed, preferably 0.5–20 mg/kg for parenteral use, 0.5–5 mg/kg for i.v. application and 10–100 mg/kg for oral use.

It is recommended to begin treatment 1 to 3 weeks before the operation and/or to continue for preferably 1 to 6 months after an operation. In the case of bone transplantation, it was shown that after 35 days new bone formation occurred in nearly all the transplants in the treated animals. It was shown, with reference to an explanted bone-tooth implant, that after treatment with Clodronate for 4 weeks (1 week before the operation and 3 weeks after), osteogenesis (bone formation) is more intensive than in patients not treated with Clodronate.

Bisphosphonates for treatment and/or prevention of loosening and migration of endoprostheses are described in WO 94/30421 A1, WO 95/28936 A1 and U.S. Pat. No. 5,646,134.

According to WO 95/30421 A1, it is recommended to prevent loosening and migration of prostheses by administering a bisphosphonate before, during and after the operation. The proposed dosage is between 0.002 and 3.40 mg/kg, preferably 0.01–2.40 mg/kg, administered continuously, i.e. daily or at cyclic intervals. Tested animals (sheep) were treated with a bisphosphonate i.v. immediately after the operation. If required the treatment should be continued at intervals, e.g. every 4 or 8 weeks. The seat of the prosthesis was checked monthly and after a year, further checks showed that the compounds gave suitable protection from loosening of prostheses. No detailed results, have been disclosed. It is also not stated what substances were used. Since the embodiments show forms of administration of pamidronate, risedronate and EB 1053, it is assumed that these compounds are preferred.

According to WO 95/28936 A1 and U.S. Pat. No. 5,646,134 bisphosphonates, preferably alendronate, are used to prevent periprosthetic bone loss by inhibiting bone resorption, and for reducing the pain associated with bone loss. Alendronate is applied preferably orally or parenterally, or alternatively the orthopaedic implant can be coated with a bisphosphonate in order to increase the fastening to the bone during the operation. The effective dosage is at 1.5 to 3000 μg/kg body weight, preferably 10 μg/kg. Bone resorption cannot be stopped completely but is considerably slowed down by treatment with higher doses of alendronate.

The object of the invention is to improve the osseointegration of endoprostheses by attaining secondary stability as quickly as possible and thus speeding up the rehabilitation of patients.

It has unexpectedly been found that osseointegration of endoprostheses, particularly joint prostheses such as knee-joint, ankle-joint or shoulder-joint endoprostheses and particularly preferably hip-joint prostheses, is accelerated and secondary stabilisation of the prosthesis is attained after only 5 weeks, preferably after 2 to 4 weeks, by short-term application, directly after the operation, of ibandronic acid (1-hydroxy-3-(N-methyl-N-pentyl)aminopropyl-1,1-diphosphonic acid) or physiologically compatible salts or esters thereof. "Osseointegration" means a direct structural and functional connection between vital bone and the surface of implants under load.

Short-term administration of ibandronate, beginning during the operation, for a period of about 2–4 weeks and 1 to 7 times per week or at cyclic intervals (depending on the individual characteristics of the patient such as age, sex and bone metabolism (osteoporotic, osteopenic, juvenile)) prevents the bone resorption caused by osteoclasts and, owing to predominance of the osteoblastic reaction, promotes an increase in bone growth on the prosthesis. The result is a rapid increase in bone mass around the prosthesis. Administration of ibandronate results in formation of a larger amount of integrated bone, earlier maturation thereof, and avoidance of osteopenia around the prosthesis. Since the duration of reduced mechanical load on the intact bones of the patient, particularly in the case of hip-joint operations, could be considerably reduced, the risk of bone atrophy was zero or negligible.

Preferably the sodium salt of ibandronic acid is used.

Ibandronic acid or pharmaceutically acceptable salts thereof, preferably the sodium salt, are well known in the art. Ibandronic acid or pharmaceutically acceptable salts thereof have been described for example in European Patent Application No. 252,504 and U.S. Pat. No. 4,927,814.

Ibandronic acid or pharmaceutically acceptable salts thereof can be administered as liquids, solids or orally in aerosol form, or enterally, parenterally, topically, nasally, pulmonary or rectally in all conventional non-toxic pharmaceutically accepted excipients, adjuvants and additives. The term "parenteral" includes subcutaneous, intravenous and intramuscular administration or infusions. Oral forms of application can be e.g. tablets, capsules, dragees, syrups, solutions, suspensions, emulsions, elixirs, etc., which can contain one or more additives out of the following groups, e.g. flavourings, sweeteners, dyes and preservatives. Oral forms of application contain the active component together with non-toxic pharmaceutically accepted excipients suitable for producing tablets, capsules, dragees etc., such as calcium carbonate, sodium carbonate, lactose, calcium phosphate or sodium phosphate; starch, mannitol, methyl cellulose, talc, highly dispersed silicic acids, higher-molecular fatty acids (such as stearic acid), peanut oil, olive oil, paraffin, miglyol, gelatine, agar, magnesium stearate, beeswax, cetyl alcohol, lecithin, glycerol, animal or vegetable fats, or solid high-molecular polymers such as polyethylene glycols. Tablets, capsules, dragees etc. can be given a suitable coating e.g. of glyceryl monostearate or glyceryl distearate in order to prevent undesired side-effects in the stomach, or to delay absorption in the gastro-intestinal tract and thus prolong the period of action. The preferred media for injection are sterile injectable aqueous or oily solutions or suspensions containing the usual additives such as stabilisers and solubilisers if required. Examples of such additives are water, isotonic common-salt solution, 1,3-butanediol, fatty acids such as oleic acid, monodiglycerides, diglycerides or miglyol. Rectal use can be made of all suitable non-irritant additives which are solid at normal temperature and liquid at rectal temperature, e.g. cocoa butter or polyethylene glycol. Usual pharmaceutical excipients can be applied in aerosol form. Creams, tinctures, gels, solutions or suspensions etc. with usual pharmaceutical additives are of use externally.

Accordingly, the present invention comprises the use of ibandronic acid or physiologically compatible salts or esters thereof for improving the osseointegration of cement-free anchored endoprostheses by short-term application directly after the operation and within two to four weeks.

++The daily i.v. equivalent dosage for ibandronate is preferably 0.1 $\mu$g/kg to 100 $\mu$g/kg body weight, preferably 1 to 100 $\mu$g/kg body weight. A daily dose of 20 to 30 $\mu$g/kg body weight is particularly preferred, and results in complete integration after only 15–20 days.

When used according to the invention, ibandronate is preferably in the form of a solution for parenteral application, containing the active substance in a proportion of 0.01–20 mg.

When using other forms of application, the dosage must be adjusted in accordance with the bioavailability of the application form.

The present invention thus relates particularly to the use of ibandronic acid or its physiological compatible salts, preferably the sodium salt, or esters to improve osseointegration of cement-free anchored endoprostheses by short-term direct post-operative application within a period of two to four weeks. Ibandronate can be used in a dose of 0.1 to 100 $\mu$g/kg body weight, preferably 1 to 100 $\mu$g/kg bodyweight. Ibandronate can also be applied as a solution for parenteral use with an active substance content of 0.01 to 20 mg. The application can be made one to seven times per week. The use of ibandronic acid as described can also be effected by intermittent cyclic application. The said uses are characterised in that the osseointegration of hip joint endoprostheses is improved. The invention also relates to the use of ibandronic acid or its physiological compatible salts or esters to establish secondary stability of hip joint endoprostheses in a period of ≦5 weeks after the operation. The use is characterised in that the secondary stability is achieved after two to four weeks.

The invention will now be explained in further detail with reference to exemplified embodiments.

EXAMPLES

Material and Method 6-month old female Spregue-Dawley rats were kept in cages and subjected to a 12-hour day and night rhythm. They had free access to food and water. The animals were kept and fed in accordance with legal regulations and the research was carried out with the approval and under the supervision of the Darmstadt Governmental Presidium.

The animals were divided at random among the various test groups. They were anaethesized by intraperitoneal administration of ketamine (75 mg/kg) and xylazine (5 mg/kg). Both back legs were sharped and disinfected with Betaisadonna solution. Medioparapatellar arthrotomy of the knee joint was carried out under aseptic conditions and the patella was laterally dislocated. The medullary canal was opened distally in the intercondylar notch and the canal was drilled with a 1.0 mm diameter Kirchner wire down to the proximal metaphysis of the femur. A titanium Kirchner wire was then inserted into the right femur and a hydroxyl apatite-coated Kirchner wire into the left femur as far as the proximal metaphysis. The access hole was closed with bone wax, the patella was replaced, the extensor apparatus of the refined leg was reconstructed, the soft tissue was adapted and the skin was closed by an intracutaneous seam. The back legs were then tested for normal post-operative movement. The animals were at liberty to move freely in their cages and the activity and the load on the hind legs was checked daily.

Ibandronate or 0.9% NaCl was administered daily as per Examples 1 and 2. After the preset treatment time the animals were euthanased in a carbon dioxide chamber and directly afterwards the two femurs were taken out, completely freed from soft tissue and fixed in alcohol for subsequent histerlogical treatment. The complete rat femurs were then displayed by X-ray in side comparison in order to judge the macromorphology and for documentation. Particular attention was given to the areas where a change in the bone occurred such as an increase or decrease in trabecular bone, a change in bone density, loosening seams on the implant, periostal or endostal changes. Evaluation in this case was purely descriptive.

Preparation of the Bone Samples

Description of production of preparations by the cut microsection technique for producing histological sections of conventional non-cuttable tissue after Prof. Donath. (K. Donath, G. Breuner: A method for the study of undecalcified bones and teeth with attached soft tissue. The Saege-Schliff (sawing and grinding) technique., J. Oral Pathology 1982, 11:318–26). The cut microsection technique is a well-tried method of preparing thin sections below 10 $\mu$m of conventional non-cuttable tissue and materials (e.g. implant-bearing long bones) for histological diagnosis.

Histology

Histological investigation of bones under the optical microscope gives knowledge about the overall structure and the distribution of bone components. Histological fuxing and production of microsections by the exact cutting and grinding system of Messrs Exakt-Apparatebau, (Norderstedt/Germany), was followed by dyeing with toluidine blue. The dyeing process is easy to carry out and the change in colour gives information about bone growth and reconstruction. Other methods of dyeing such as haematoxylin-eiosine dyeing, van Gieson dyeing or Masson-Golner dyeing, give good representations of the is embedded tissue. The resulting preparations were then documented by photography. Quantitative evaluation of the results was by histomorphometry.

Histomorphometry

The bone-covered area on the metal implant was shown and calculated by histomorphometry, using special software.

Example 1

1a) Time sequence of osseointegration of titanium implants and hydroxyl apatite-coated implants in the bone of 6 month-old Spregue Dawley rats.

1b) Time sequence of osseointegration of titanium implants and hydroxyl apatite-coated implants in the bone of 6 month-old Sprague Dawley rats after administration of 1 μg FAE/kg/d, 5 μg FAE/kg/d and 25 μg FAE/kg/d ibandronate (FAE=free acid equivalent, i.e. all dosages are related thereto.

Four experimental groups were formed and the animals were distributed at random among them. At each time, 2 animals in each group were operated and killed.

| | |
|---|---|
| 1) Control group: | Daily subcutaneous administration of 0.9% NaCl after implantation of the implants |
| 2) Experimental group 1: (1 μg FAE/kg/d) | Daily subcutaneous administration of 1 μg FAE/kg/d ibandronate after implantation of the implants |
| 3) Experimental group 2: (5 μg FAE/kg/d) | Daily subcutaneous administration of 5 μg FAE/kg/d ibandronate after implantation of the implants |
| 4) Experimental group 3: (25 m4) Experimental group 3: (25 μg FAE/kg/d) | Daily subcutaneous administration of 25 μg FAE/kg/d ibandronate after implantation of the implants |

The animals were killed at 11 defined dates (days after implantation) as follows: 0, 4, 7, 10, 14, 18, 22, 27, 32, 37, 42.

The other procedure was in accordance with the description of the experiments.

Evaluation:

Osseointegration of the group treated with ibandronate was appreciably improved compared with the untreated group. Nearly complete ingrowth occurred after 37 days in the untreated group whereas in the group treated with 25 μg FAE/kg/d ibandronate, complete integration occurred surprisingly after only 18 days—i.e. a temporal advantage of more than 50% after treatment with ibandronate.

Example 2

2a) Significant differences between osseointegration of titanium implants and hydroxyl apatite-coated implants in the bone of 6-month old rats at a defined time after administration of 1 μg FAE/kg/d, 5 μg FAE/kg/d and 25 μg FAE/kg/d ibandronate compared with an untreated control group.

2b) Significant differences between osseointegration of titanium implants and hydroxyl apatite-coated implants in the bone of 6-month old rats at a defined time after bolus administration of ibandronate at a total dose of 1 μg FAE/kg/d, 5 μg FAE/kg/d and 25 μg FAE/kg/d ibandronate once per day, compared with an untreated control group.

2c) Significant differences in osseointegration of titanium implants and hydroxyl apatite-coated implants in the bone of 6-month old rats at a defined time between a bolus administration and a cumulative administration over the entire period.

Seven experimental groups were formed and evaluated after 15–20 days, preferably after 18 days. The defined date was obtained from Example 1 (using a statistically sufficient number of 15 experimental animals, showing a significant difference between the groups ($p<0.01$)).

| | |
|---|---|
| 1) Control group: | Subcutaneous administration of 0.9% NaCl for 15–20 days after the operation |
| 2) Experimental group: | Subcutaneous administration of 1 μg FAE/kg/d ibandronate for 15–20 days after the operation |
| 3) Experimental group: | Subcutaneous administration of 5 μg FAE/kg/d ibandronate for 15–20 days after the operation |
| 4) Experimental group: | Subcutaneous administration of 25 μg FAE/kg/d ibandronate for 15–20 days after the operation |
| 5) Experimental group: | Subcutaneous bolus administration of 1 μg FAE/kg/d ibandronate for 15–20 days after the operation |
| 6) Experimental group: | Subcutaneous bolus administration of 5 μg FAE/kg/d ibandronate for 15–20 days after the operation |
| 7) Experimental group: | Subcutaneous bolus administration of 25 μg FAE/kg/d ibandronate for 15–20 days after the operation |

Evaluation:

2a) Very significant differences between the treated groups and the control group (50% increase after administration of 25 μg FAE/kg/d ibandronate compared with the control group).

2b) Very significant differences between the bolus-treated groups and the control group ((50% increase after administration of 25 μg FAE/kg/d ibandronate compared with the control group).

2c) No significant differences were found between bolus administration and cumulative administration. Consequently a single bolus administration has appreciable clinical advantages.

What is claimed is:

1. A method of improving the osseointegration of a cement-free anchored endoprostheses comprising application of from about 0.1 μg/kg to about 100 μg/kg body weight/day of ibandronic acid or physiologically compatible salts or esters thereof commencing during surgery or shortly thereafter and continuing for about two to four weeks after an operation to implant the endoprosthesis.

2. The method according to claim 1 wherein ibandronate in solution for is applied for parental application with a content of active substance of 0.01 to 20 mg.

3. The method according to claim 2, wherein application is made 1 to 7 times per week.

* * * * *